United States Patent [19]
Baker et al.

[11] Patent Number: 5,504,188
[45] Date of Patent: Apr. 2, 1996

[54] PREPARATION OF STABLE ZINC INSULIN ANALOG CRYSTALS

[75] Inventors: Jeffrey C. Baker; Nancy D. Carter; Bruce H. Frank, all of Indianapolis, Ind.

[73] Assignee: Eli Lilly and Company, Indianapolis, Ind.

[21] Appl. No.: 260,647

[22] Filed: Jun. 16, 1994

[51] Int. Cl.$^6$ .............................. A61K 38/28; C07K 14/62
[52] U.S. Cl. ................................................. 530/304; 514/3
[58] Field of Search ................... 530/304; 514/3

[56] References Cited

U.S. PATENT DOCUMENTS

| | | |
|---|---|---|
| 2,143,590 | 1/1939 | Scott et al. . |
| 2,626,228 | 1/1953 | Petersen . |
| 2,920,014 | 1/1960 | Petersen et al. . |
| 3,719,655 | 3/1973 | Jackson . |
| 4,959,351 | 9/1990 | Grau ............................. 514/4 |
| 5,028,587 | 7/1991 | Dörschug et al. ........................ 514/3 |
| 5,149,777 | 9/1992 | Hansen et al. ........................... 530/303 |
| 5,164,366 | 11/1992 | Balschmidt et al. ....................... 514/3 |

FOREIGN PATENT DOCUMENTS 0214826  3/1987  European Pat. Off. .

OTHER PUBLICATIONS

Fullerton, et al., *Biochim, Biophys. Acta*, 214, 141–147 (1970).
*Diabetologia*, 30, 503A (1987).
Brange, et al., *Nature*, 333:16, 679–682 (Jun. 1988).
Brange, et al., *Diabetes Care*, 13:9, 923–954 (Sep. 1990).
Brange, et al., *Structural Biology*, 1, 934–940 (1991).
Brange, *Galenics of Insulin: The Physico-chemical and Pharmaceutical Aspects of Insulin and Insulin Preparations*, Springer-Verlag Berlin Heidelberg, Germany (1987).
Scott, *Biochemical Journal*, 28:4, 1592–1602 (Apr. 28, 1934).
Brems, et al., *Protein Engineering*, 5:6, 527–533 (1992).
Wollmer, et al., *Biol. Chem. Hoppe–Seyler*, 370, 1045–1053 (Sep. 1989).
Wollmer, et al., *Phenol–Promoted Structural Transformation of Insuline in Soluntion* from the 2nd Assisi International Symposium on Advanced Models for the Therapy of Insulin–Dependent Diabetes, 903–911 (Apr. 1986).
Harding, et al., *The Crystal Structure of Insulin: II. An Investigation of Rhombohedral Zinc Insulin Crystals and a Report of Other Crystalline Forms* Chemical Crystallography Laboratory, South Parks Road, Oxford, England (Nov. 8, 1965).
Derewenda, et al., *Nature*, 338, 594–596 (Apr. 13, 1989).
Brems, et al., *Protein Engineering*, 5:6, 519–525 (1992).
Howey, et al., *Diabetes*, 43, 396–402 (Mar. 1994).
*Diabetes*, 41, Suppl. 1, 192A (1992).
Brems, et al., *Protein Engineering*, 5:6, 519–525 (1992).
Heinemann, et al., *Diabetologia*, 33, 384–386 (1990).
Kirk–Othmer, *Encyclopedia of Chemical Technology 13*, 607–614 (1981).
Bruce H. Frank, Text aned Slide copies of lecture given at the Conference on Insulin, Self Association and Conformational Studies on Human Proinsulin and Insulin Analogs, University of York, Aug. 29–Sep. 1, 1989.

*Primary Examiner*—Jill Warden
*Assistant Examiner*—Benet Prickril
*Attorney, Agent, or Firm*—Steven P. Caltrider; David E. Boone

[57] ABSTRACT

The present invention discloses a process of preparing a crystalline insulin analog. The process is useful in the purification and manufacture of Lys$^{B28}$Pro$^{B29}$-human insulin. Lys$^{B28}$Pro$^{B29}$-human insulin is useful in the treatment of diabetes.

11 Claims, No Drawings

PREPARATION OF STABLE ZINC INSULIN ANALOG CRYSTALS

FIELD OF INVENTION

The present invention relates to a monomeric analog of human insulin. More specifically, the present invention relates to a process of preparing a crystalline insulin analog. The process is useful in the purification and manufacture of Lys$^{B28}$Pro$^{B29}$-human insulin. Lys$^{B28}$Pro$^{B29}$-human insulin is useful in the treatment of diabetes.

BACKGROUND OF THE INVENTION

Since the introduction of insulin in the 1920's, continuous strides have been made to improve the treatment of diabetes mellitus. Major advances have been made in insulin purity and availability. Various formulations with different time-actions have also been developed. Despite these improvements, subcutaneous injection therapy still falls short of providing the patient with convenient regulation and normalized glycemic control. Frequent excursions from normal glycemia levels over a patient's lifetime lead to hyper- or hypoglycemia, and long term complications including retinopathy, neuropathy, nephropathy, and micro- and macroangiopathy.

To help avoid extreme glycemic levels, diabetics often practice multiple injection therapy whereby insulin is administered with each meal. However, this therapy has not yet been optimized. The most rapid-acting insulin commercially available peaks too late after injection and lasts too long to optimally control glucose levels. Recently, considerable effort has been devoted to create insulin formulations and insulin analog formulations that alter the kinetics of the subcutaneous absorption process.

Because all commercial pharmaceutical formulations of insulin contain insulin in the self-associated state and predominately in the zinc-hexamer form, it is believed that the rate-limiting step for the absorption of insulin from the subcutaneous injection depot to the bloodstream is the dissociation of the self-aggregated insulin hexamer. To accelerate this absorption process, monomeric insulin analogs have been developed. These monomeric analogs possess a comparatively more rapid onset of activity than insulin while retaining the biological activity of native human insulin. They provide a rapid absorption to place injection time and peak action of insulin into closer proximity with postprandial glucose excursion associated in the response to a meal.

The present invention provides a novel process of preparing crystals of one such monomeric analog, Lys$^{B28}$Pro$^{B29}$-human insulin (Lys$^{B28}$Pro$^{B29}$-hI). Lys$^{B28}$Pro$^{B29}$-hI is disclosed in U.S. patent application Ser. No. 07/388,201 (EPO publication number 383 472). However, U.S. patent application Ser. No. 07/388,201 does not disclose a commercially viable process of preparing crystalline Lys$^{B28}$Pro$^{B29}$-hI.

The crystallization of insulin is well known in the art. Initial discoveries date back to 1926 when Abel crystallized insulin in the isoelectric region from a solution buffered with brucine, pyridine, and ammonium acetate. Abel J. J., *Proc. Nat'l Acad Sci. U.S.* 12: 132 (1926). Peterson, et al. in U.S. Pat. No. 2,920,104 describes insulin crystals and preparations and processes for producing them. Today, the commercial process for crystallizing insulin comprises adjusting the basicity of a insulin solution comprising 0.25N acetic acid, about 2 g/l insulin, and 2% zinc to pH 5.9 to 6.0 with a base, preferably ammonium hydroxide. Jens Brange, GALENICS OF INSULIN, Springer-Verlag (1987). Host significantly, when Lys$^{B28}$Pro$^{B29}$-hI is subjected to the conditions that permit human insulin to form either zinc crystals, no such crystallization occurs.

The present invention provides a process of crystallizing Lys$^{B28}$Pro$^{B29}$-hI unique to the molecule, that is, the conditions do not crystallize human insulin. The process prepares high quality, high yield zinc crystals on a large scale. The crystals provide a stable, solid form of the molecule. Crystalline solids are particularly advantageous because they are more easily characterized, purified, and more pharmaceutically elegant than solids that are amorphous. Accordingly, the process is suitable for commercial application.

SUMMARY OF THE INVENTION

This invention provides a process of preparing a crystalline Lys$^{B28}$Pro$^{B29}$-human insulin, which comprises: crystallizing Lys$^{B28}$Pro$^{B29}$-human insulin from a solution comprising Lys$^{B28}$Pro$^{B29}$-human insulin, zinc, at least 0.3N of an organic acid selected from the group consisting acetic, citric, or glycine, and a phenolic at a pH of about 5.5 to about 6.5.

DETAILED DESCRIPTION AND PREFERRED EMBODIMENTS

As noted above, the invention provides a process for preparing crystalline Lys$^{B28}$Pro$^{B29}$-human insulin. The term "Lys$^{B28}$Pro$^{B29}$-human insulin" or "Lys$^{B28}$Pro$^{B29}$-hI" is a fast-acting insulin analog that is less prone to dimerization or self-association. Lys$^{B28}$Pro$^{B29}$-hI is human insulin wherein proline at position B28 of the B-chain is substituted with Lysine; and Lysine at position B29 of the B-chain is substituted with Proline as described in U.S. patent application Ser. No. 07/388,201 (EPO publication number 383 472), herein incorporated by reference.

All amino acid abbreviations used in this disclosure are those accepted by the United States Patent & Trademark Office as set forth in 37 C.F.R. §1.822(b)(2).

The term "phenolic" or "phenolic derivative" as used herein collectively means phenol, resorcinol, m-cresol, or methyl-p-hydroxybenzoate, or mixtures thereof.

The term "crystallizing" as used herein refers to the formation of Lys$^{B28}$Pro$^{B29}$-human insulin crystals.

The term "physiologically tolerated base" is known to one skilled in the art. A physiologically tolerated base includes sodium hydroxide, potassium hydroxide and ammonium hydroxide. Preferably, the base is ammonium hydroxide.

The formation of crystalline insulin has been extensively studied. Human insulin is commercially crystallized in the presence of 0.25N acetic acid, 1.6 to 2.1 g/l insulin, and 2% zinc at a pH of 5.95 to 6.05. The crystallization proceeds by approaching the crystallization from the acidic side with the addition of a base, typically sodium hydroxide. Most unexpectedly, soluble Lys$^{B28}$Pro$^{B29}$-hI does not crystallize under the known conditions of preparing insulin crystals. Lys$^{B28}$Pro$^{B29}$-hI is designed to minimize self-association and aggregation. The observation that Lys$^{B28}$Pro$^{B29}$-hI does not aggregate was initially noted by Brems et al., *Protein Engineering*, 5:6, 527–533 (1992). Minimal self-association and aggregation, which cause the analog to be monomeric, are believed to be responsible for the failure of Lys$^{B28}$Pro$^{B29}$-hI to crystallize under the conditions developed for insulin.

The present invention describes conditions under which $Lys^{B28}Pro^{B29}$-hI crystallizes with zinc and a phenolic compound to form a stable, crystalline solid. Preferred phenolics are selected from the group consisting of phenol, resorcinol, or a mixture thereof Both the zinc and the phenolic are critical to achieve crystallization.

A solution of $Lys^{B28}Pro^{B29}$-hI is prepared by dissolving the insulin analog in an aqueous diluent. The concentration of $Lys^{B28}Pro^{B29}$-hI is about 1.8 g/l to about 2.5 g/l. Most preferably, the concentration of analog is about 2 g/l. Dissolution may be aided by what is commonly known as an acid dissolution, i.e., the pH is lowered no about 3.0 to 3.5 with a physiologically tolerated acid, preferably hydrochloric acid. Other physiologically moderated acids include acetic acid, citric acid, and phosphoric acid.

The concentration of organic acid selected from the group consisting acetic, citric, or glycine is at least 0.3N; below 0.3N a largely amorphous product results. Preferably, $Lys^{B28}Pro^{B29}$-hI is dissolved in about 0.8 to about 1.2N acetic acid; most preferably, 1N acetic acid.

The concentration of zinc added is such that the final concentration is about 40 mg to about 400 mg per gram of analog. Zinc is preferably added as a salt. Representative examples of zinc salts include zinc acetate, zinc bromide, zinc chloride, zinc fluoride, zinc iodide and zinc sulfate. The skilled artisan will recognize that there are many other zinc salts that also might be used in the process of the present invention. Preferably, zinc acetate or zinc chloride is used because these salts do not add new chemical ions to commercially accepted processes. The optimal concentration of zinc in the crystallization is from about 100 to about 300 mg per gram of $Lys^{B28}Pro^{B29}$-hI.

The crystallization conditions are sensitive to the phenolic, base and concentration of zinc; that is, one skilled in the art carrying out the process would adjust the parameters defined herein to achieve well-defined crystals. The optimum conditions for each phenolic-base combination varies within the ranges disclosed. Preferably, the phenolic is phenol at a concentration of about 0.15 to about 0.25% (v/v, final concentration). More preferably, phenol at a concentration of 0.2%.

The manner in which the $Lys^{B28}Pro^{B29}$-hI is dissolved in the solution or the order in which the phenolic, zinc, and $Lys^{B28}Pro^{B29}$-hI are added to the solution is not critical to the present process. However, it is critical that the phenolic interacts with the $Lys^{B28}Pro^{B29}$-hI below the isoelectric point of $Lys^{B28}Pro^{B29}$-hI. Accordingly, crystallization may be initiated by either the addition of zinc or by the adjusting the basicity of the solution from an acidic pH to about 5.5 to 6.5 with the addition of a physiologically tolerated base. Physiologically tolerated bases include sodium hydroxide, potassium hydroxide and ammonium hydroxide. Preferably, the base is ammonium hydroxide.

The crystallization may be carried out by adjusting the basicity of a solution comprising $Lys^{B28}Pro^{B29}$-human insulin, zinc, at least 0.3N of an organic acid selected from the group consisting acetic, citric, or glycine, and a phenolic to a pH of about 5.5 to about 6.5 with a physiologically tolerated base. Preferably, the pH is adjusted to a pH of about 5.9 to 6.2. The crystals are formed when the pH is adjusted.

More preferably, $Lys^{B28}Pro^{B29}$-hI is dissolved in about 1N acetic acid (if necessary to aid in the dissolution, the pH may be adjusted to 3.0–3.5). The phenolic is then added to the solution and allowed to equilibrate. The pH of the solution is adjusted to a pH of about 5.5 to about 6.5 with a physiologically tolerated base. Preferably, the base is ammonium hydroxide and the pH is adjusted to a pH of about 5.9 to 6.2. The crystallization is then initiated by the addition of zinc.

Employing either means for crystallizing, the crystals form with or without agitation and may be collected and washed. Preferably, the crystallization is carried out with agitation. $Lys^{B28}Pro^{B29}$-hI may be recrystallized, if required, to facilitate filtration. The crystals may be collected and dried by conventional means. If the crystals are collected by filtration, additional zinc may be added to the filtrate, or the mother liquor, to further recover $Lys^{B28}Pro^{B29}$-hI. The crystals prepared in accordance with the present invention are high quality and in high yield on a commercial scale. The crystals provide a stable solid form of the bulk drug substance suitable for holding and dispensing to fill/finish operations. The crystallization procedure does not alter the purity or aggregation kinetics of the material.

The temperature of the crystallization is not critical. The temperature range acceptable is from about 4° C. to about 26° C. Preferably, the temperature is about 22° C. to about 24° C.

$Lys^{B28}Pro^{B29}$-hI can be prepared by any of a variety of recognized peptide synthesis techniques including classical (solution) methods, solid phase methods, semi synthetic methods, and more recent recombinant DNA methods. For example, Chance et al., U.S. patent application Ser. No. 07/388,201, EPO publication number 383 472, discloses the preparation of $Lys^{B28}Pro^{B29}$-human insulin.

The following examples are provided merely to further illustrate the preparation of the insulin analogs and the invention. The scope of the invention is not construed as merely consisting of the following examples.

EXAMPLE 1

A process stream 846.5 base grams of $Lys^{B28}Pro^{B29}$-hI in 116 L of acetic acid buffer was diluted to an absorbance at 276 nm of 2.25 with purified water (260.6 L) and glacial acetic acid (19.44 L) in a stainless steel drum to a final concentration of 1N acetic acid. Liquified phenol was added to the solution at 2 mL/L (792 mL total), and the pH of the resulting solution was confirmed to be below pH 3. The solution was adjusted to pH 6.01 by the addition of 24 L of ammonium hydroxide and then warmed to 22° C. After warming, 5.35 L of zinc chloride solution (2% w/v in water) were added. The pH of the solution was reconfirmed to be in the desired range (5.9–6.1) and the solution agitated for 12 hours. The solution was chilled to 8° C., agitation was stopped, and the crystals were allowed to settle for over 18 hours at 2°–8° C. After the crystals had settled, 370 L of the supernatant was decanted and the remaining supernatant and crystals bed were transferred into a smaller drum for additional settling using a portion of the decanted supernatant to rinse the original drum. After 14 hours of settling time, 61 L of supernatant was decanted leaving approximately 9 L of wet crystal bed and supernate.

The crystals were slurried in this volume and centrifuged in 6 one liter centrifuge bottles at 4000 rpm (approximately 4000×G) in a DPR6000 centrifuge for 45 minutes. Two loads were required to get all of the crystal slurry into the 6 bottles. The centrate was decanted. The crystals (approximately 250 mL per bottle) were slurried with 500 mL of purified water per centrifuge bottle and recentrifuged at 4000 rpm for 45 minutes. The crystals were then reslurried in the centrifuge bottles with approximately 500 ml of chilled (2°–8° C.) Alcohol SD No. 3A Absolute per bottle and recentrifuged at 4000 rpm for 15 minutes. The alcohol centrate was decanted and the alcohol wash was repeated twice more. The alcohol washed crystals (1.9 kg wet weight) were dried under vacuum.

EXAMPLE 2

A $Lys^{B28}Pro^{B29}$-hI solution at approximately 2 g/L is prepared to a final concentration of 1M acetic acid (as determined by absorbance at 280 nm). The addition of liquefied phenol (3.3 mL/L of solution) to the solution is followed by the adjustment of the pH to 5.9–6.2 with concentrated ammonium hydroxide and the addition of zinc chloride as a 2% (w/v) or 20% (w/v) solution to a final concentration of 40–160 mg zinc chloride per gram of $Lys^{B28}Pro^{B29}$-hI. The resulting crystals are allowed to settle, and the mother liquor is removed by decantation followed by centrifugation. The crystals are washed by sequential slurrying and centrifugation in water, and finally absolute ethanol prior to drying under vacuum. A second crop of crystals may be generated by adding zinc to the mother liquor to a limit of 160 mg/g of $Lys^{B28}Pro^{B29}$-hI.

EXAMPLE 3

$Lys^{B28}Pro^{B29}$-human insulin (222 mg) was dissolved in 100 ml of Milli-Q water. The solution was determined to contain 2.0 mg of $Lys^{B28}Pro^{B29}$-hI per milliliter of solution by HPLC analysis. The solution was clarified by adjusting to approximately pH 3.0 with 10% HCl. Four 5 ml aliquots were withdrawn and made 1N in acetic acid by the addition of glacial acetic acid and the pH was confirmed to be below 3.5. Ten microliters of liquified phenol followed by six microliters of zinc chloride solution (20% w/v in water) were added to each sample. The pH was adjusted to 6.0 by the addition of either concentrated ammonium hydroxide, sodium hydroxide (10% solution w/v), or potassium hydroxide (10% solution w/v). The solutions were stirred for approximately 15 minutes and then allowed to stand, covered, at room temperature. After approximately 2 hrs, well defined rhombohedral crystals were observed in all three solutions with crystals forming most rapidly in the solution adjusted with potassium hydroxide.

EXAMPLE 4

Approximately 42 mg of $Lys^{B28}Pro^{B29}$-hI were dissolved in either 20 ml of Milli-Q water containing 1.2 ml glacial acetic. Forty four microliters of liquefied phenol was added to the first sample and 34 microliters of liquified phenol was added to the second. In both cases the pH was adjusted to 6.0 with the addition of concentrated ammonium hydroxide, followed by the addition of forty five microliters of zinc chloride solution (20% w/v in water). The solution was stirred for approximately 5 minutes at which time they were allowed to stand, covered, at room temperature. After approximately 24 hrs well defined rhombohedral crystals were observed.

EXAMPLE 5

$Lys^{B28}Pro^{B29}$-human insulin (222 mg) was dissolved in 100 ml of Milli-Q water and the solution was determined to contain 2.0 mgs of $Lys^{B28}Pro^{B29}$-hI per milliliter of solution by HPLC analysis. The solution was clarified by adjustment to approximately pH 3.0 with 10% HCl. Four 5 ml aliquots were withdrawn and made 1N in acetic acid by the addition of glacial acetic acid and the pH was confirmed to be below 3.5. Either m-cresol (12 µl), phenol (10 µl), resorcinol (2.1 µl of a 100 mg/ml solution in water), or methyl paraben (1.6 ml of a 10 mg/ml solution in water) was added to an aliquot generating crystallization solutions having similar molar ratios of peptide to phenolic. Six microliters of zinc chloride solution (20% w/v in water) was added to each sample and the the pH was adjusted to 6.0 with concentrated ammonium hydroxide. The solutions were stirred for approximately 15 minutes and then allowed to stand, covered, at room temperature. After approximately 24 hrs well defined rhombohedral crystals were observed in the solutions containing phenol. The solution containing methylparaben produced some poorly defined planar crystals. The solutions containing m-cresol and resorcinol did not produce crystals under these conditions.

A similar procedure was executed using one tenth the amount of resorcinol and adjusting with sodium hydroxide (10% w/v solution), well defined, rhombohedral crystals resulted. This example demonstrates that through routine optimization of the conditions well defined crystals may be formed with the phenolics.

EXAMPLE 6

$Lys^{B28}Pro^{B29}$-hI (222 mg) was dissolved in 100 ml of Milli-Q water and the solution was determined to contain 2.0 mg of $Lys^{B28}Pro^{B29}$-hI per milliliter of solution by HPLC analysis. The solution was clarified by adjustment to approximately pH 3.0 with 10% HCl. One 5 ml aliquot was withdrawn and made 0.25N in acetic acid by the addition of glacial acetic acid and the pH was confirmed to be below 3.5. Twenty microliters of zinc chloride solution (2% w/v in water) to the sample. The pH was adjusted to 6.0 by the addition concentrated ammonium hydroxide. The solution was stirred for approximately 15 minutes at which time it was allowed to stand, covered, at room temperature. After approximately 24 hrs no crystals were observed in solution but an amorphous precipitate had settled to the bottom of the vessel.

As a control, another 5 ml aliquot was withdrawn and subjected to the ammonium hydroxide procedure described in Example 1. Well defined rhombohedral crystals of $Lys^{B28}Pro^{B29}$-hI were formed. When human insulin (2.3 mg/ml in 1N acetic acid) was subjected to the conditions described in Example 1 which used ammonium hydroxide, no crystals were formed within 7 days.

This experiment demonstrates that conditions routinely used in the crystallization of biosynthetic human insulin are inappropriate for the crystallization of the $Lys^{B28}Pro^{B29}$-human insulin and similarly that the crystallization conditions described for the crystallization of $Lys^{B28}Pro^{B29}$-hI will not produce crystals of human insulin.

EXAMPLE 7

In a manner analogous to Example 1, the crystallization was carried out substituting 1N citric acid for 1N acetic acid. The crystallization produced well-defined crystals of $Lys^{B28}Pro^{B29}$-hI.

We claim:

1. A process of preparing crystalline $Lys^{B28}Pro^{B29}$-human insulin, which comprises: crystallizing $Lys^{B28}Pro^{B29}$-human insulin from a solution comprising $Lys^{B28}Pro^{B29}$-human insulin, zinc, at least 0.3N of an organic acid selected from the group consisting acetic, citric, or glycine, and a phenolic at a pH of about 5.5 to about 6.5.

2. The process of claim 1, wherein the concentration of $Lys^{B28}Pro^{B29}$-human insulin is about 1.8 to about 2.5 g/l.

3. The process of claim 2, wherein the phenolic is phenol.

4. The process of claim 3, wherein the concentration of zinc is about 40 mg/gm of $Lys^{B28}Pro^{B29}$-human insulin to about 400 mg/gm of $Lys^{B28}Pro^{B29}$-human insulin.

5. The process of claim 4, wherein the concentration of phenol is about 0.15% to 0.25% on a volume basis.

6. The process of claim 5, wherein the pH is about 5.9 to about 6.2.

7. The process of claim 6, wherein the $Lys^{B28}Pro^{B29}$-human insulin is recrystallized.

8. The process of claim 1, wherein the crystallization is initiated by adjusting the basicity of the solution comprising $Lys^{B28}Pro^{B29}$-human insulin, zinc, at least 0.3N acetic acid, and a phenolic; to a pH of about 5.9 to about 6.2 with a physiologically tolerated base.

9. The process of claim 1, wherein the crystallization is initiated by the addition of zinc to the solution at pH 5.9 to 6.2.

10. A process of preparing crystalline $Lys^{B28}Pro^{B29}$-human insulin, which comprises:

(a) adding phenol at 0.15% to 0.25% on a final volume basis to a solution of $Lys^{B28}Pro^{B29}$-hI solution at about 1.8 to 2.5 g/L in about 1N acetic acid;

(b) adjusting the pH to about 5.9 to about 6.2 with ammonium hydroxide; and (c) adding a zinc salt solution to a final concentration of about 40 to about 400 mg zinc chloride per gram of $Lys^{B28}Pro^{B29}$-hI.

11. The process of claim 10, wherein the zinc salt is zinc chloride.

* * * * *

UNITED STATES PATENT AND TRADEMARK OFFICE
CERTIFICATE OF CORRECTION

PATENT NO. : 5,504,188
DATED : April 2, 1996
INVENTOR(S) : Jeffrey C. Baker, et al.

It is certified that error appears in the above-indentified patent and that said Letters Patent is hereby corrected as shown below:

Column 3, line 14, reads _"physiologically moderated"_ should read -physiologically tolerated-.

Signed and Sealed this

Seventh Day of October, 1997

Attest:

BRUCE LEHMAN

Attesting Officer

Commissioner of Patents and Trademarks